US009039678B2

(12) United States Patent
Saxena et al.

(10) Patent No.: US 9,039,678 B2
(45) Date of Patent: May 26, 2015

(54) MICROMECHANICAL FORCE DEVICES FOR WOUND HEALING ACCELERATION

(75) Inventors: Vishal Saxena, Somerville, MA (US); Dennis Orgill, Belmont, MA (US); Roberto Rangel, Catonsville, MD (US)

(73) Assignee: The Brigham and Women's Hospital, INC, Boston, MA (US)

( * ) Notice: Subject to any disclaimer, the term of this patent is extended or adjusted under 35 U.S.C. 154(b) by 853 days.

(21) Appl. No.: 12/418,279

(22) Filed: Apr. 3, 2009

(65) Prior Publication Data

US 2009/0270843 A1 Oct. 29, 2009

Related U.S. Application Data

(60) Provisional application No. 61/041,952, filed on Apr. 3, 2008.

(51) Int. Cl.

| | |
|---|---|
| ***A61M 27/00*** | (2006.01) |
| *A61M 1/00* | (2006.01) |
| *A61F 13/02* | (2006.01) |
| *A61M 39/02* | (2006.01) |
| *A61B 17/50* | (2006.01) |

(52) U.S. Cl.
CPC ........... *A61M 1/0037* (2013.01); *A61M 1/0009* (2013.01); *A61M 1/0088* (2013.01)

(58) Field of Classification Search
CPC ....... A61M 1/00; A61M 39/02; A61M 27/00; A61F 13/00; A61F 13/02; A61B 17/50
USPC .................................................. 604/540–544
See application file for complete search history.

(56) References Cited

U.S. PATENT DOCUMENTS

| | | | | |
|---|---|---|---|---|
| 3,279,653 A * | 10/1966 | Pfleger | .......................... | 222/642 |
| 4,278,089 A | 7/1981 | Huck et al. | | |
| 4,404,924 A | 9/1983 | Goldberg et al. | | |
| 4,969,880 A | 11/1990 | Zamierowski | | |
| 5,071,409 A * | 12/1991 | Rosenberg | .................... | 604/119 |
| 5,478,316 A * | 12/1995 | Bitdinger et al. | ............. | 604/135 |
| 5,636,643 A | 6/1997 | Argenta et al. | | |
| 5,645,081 A | 7/1997 | Argenta et al. | | |
| 2007/0100277 A1* | 5/2007 | Shippert | ......................... | 604/27 |

FOREIGN PATENT DOCUMENTS

EP 0584714 A1 * 8/1993

OTHER PUBLICATIONS

Saxena, V., et al., "Vacuum-assisted closure: microdeformations of wounds and cell proliferation." Plast Reconstr Surg, 2004. 114(5): p. 1086-1096; discussion 1097-8.

Akhyari, P., et al., "Mechanical stretch regimen enhances the formation of bioengineered autologous cardiac muscle grafts." Circulation, 2002. 106(12 Suppl 1): p. 1137-1142.

(Continued)

*Primary Examiner* — Tatyana Zalukaeva
*Assistant Examiner* — Ilya Treyger
(74) *Attorney, Agent, or Firm* — Quarles & Brady, LLP

(57) ABSTRACT

An apparatus provides micromechanical forces on a wound bed to accelerate healing of a wound. The apparatus includes a pressure chamber having a substantially airtight plunger and an inlet fluidly connected to a first end of a conduit. A constant force spring is operatively connected to apply a constant force to the plunger. A suction cup is in fluid communication with a second end of the conduit.

4 Claims, 8 Drawing Sheets

(56) References Cited

OTHER PUBLICATIONS

Ilizarov, G.A., "The tension-stress effect on the genesis and growth of tissues. Part I. The influence of stability of fixation and soft-tissue preservation." Clin Orthop Relat Res, 1989(238): p. 249-281.

Ilizarov, G.A., "The tension-stress effect on the genesis and growth of tissues: Part II. The influence of the rate and frequency of distraction." Clin Orthop Relat Res, 1989(239): p. 263-285.

Saxena, V., "Genomic Response, Bioinformatics, and Mechanics of the Effects of Forces on Tissues and Wound Healing, in Mechanical Engineering." 2005, Massachusetts Institute of Technology: Cambridge. p. 167.

Meyer, D.C. et al., "Weight-loaded syringes as a simple and cheap alternative to pumps for vacuum-enhanced wound healing." Plast Reconstr Surg, 2005. 115(7): p. 2174-2176.

* cited by examiner 420
422
424b
406
426
424a
402
400

MICROMECHANICAL FORCE DEVICES FOR WOUND HEALING ACCELERATION

RELATED APPLICATION

This patent application claims the benefit of priority under 35 U.S.C. §119 of U.S. Provisional Patent Application No. 61/041,952 filed on Apr. 3, 2008, the contents of which are incorporated herein by reference.

FIELD OF THE INVENTION

The present invention relates to micromechanical force devices for healing wounds, and more particularly, to devices for applying pressure to accelerate healing of wounds.

DESCRIPTION OF RELATED ART

A variety of devices are known in the art for providing micromechanical force therapy to wounds. Of such devices, many are directed to devices that apply suction to wound beds to accelerate healing of wounds. Exemplary wounds which can be treated with micromechanical force therapy include diabetic foot ulcers, venous stasis ulcers, pressure ulcers, traumatic wounds, surgical wounds, infected wounds, burns, radiation wounds, wounds with exposed hardware, degloving injuries, and venomous injuries. Typically, a wound is treated and covered with an open cell foam. A drape, typically made of polyurethane in the form of a suction cup, is placed over the foam. A vacuum source, usually an electric pump, is connected to the suction cup to provide constant or constant cycling pressure therapy to the wound bed. This therapy can allow for a degree of healing of wounds in one or two days that would normally require on the order of one month without the therapy.

It is well known that cells respond to their chemical environment. For example, different autocrine, paracrine, and endocrine molecules travel to the wound bed to create the wound healing response. This response is seen in changes in the gene expression profile of cells that reside in the wound bed. However, the mechanical environment of the cell (comprising both the mechanical state of the cell surroundings and mechanical stimuli to the cell) also causes a change in the gene expression profile of resident wound cells, thereby causing a response to forces.

Generally, known devices used for applying micromechanical therapy to wounds involve an electrical pump that is used to apply sub-atmospheric pressure to a suction cup over the wound site. The pump is typically bulky and the overall device limits mobility of individuals undergoing micromechanical therapy.

Conventional methods and systems of providing micromechanical therapy to wounds have generally been considered satisfactory for their intended purpose. However, there remains an ever present need to advance the state of the art for reducing the size, and increasing the mobility and convenience of devices for applying micromechanical therapy. There also remains a need in the art for devices and methods for providing micromechanical therapy that are inexpensive and easy to make and use. The present invention provides a solution for these problems.

SUMMARY OF THE INVENTION

In accordance with one aspect, the subject invention provides a new and useful apparatus for providing micromechanical forces on a wound bed to accelerate healing of a wound. The apparatus includes a first pressure chamber communicating with a first vacuum source. The first pressure chamber also communicates with a suction cup. A second pressure chamber communicates with a second vacuum source. The second pressure chamber is operably connected with the first pressure chamber through a door. A plunger is in fluid contact with the first chamber and is operatively connected to the door. The plunger is configured and adapted to maintain a substantially constant pressure in the first chamber by moving the door between a first position and a second position. In the first position, and the first and second chambers are in fluid communication with one another. In the second position, the first and second chambers are in fluid isolation from one another.

In accordance with another embodiment, sensing and actuating means are provided to maintain a substantially constant pressure in the first chamber by moving the door between the first and second positions described above. The sensing and actuating means can include any suitable combination of electrical or mechanical sensors, control systems, motors, and/or actuators.

The invention also provides an apparatus for providing micromechanical forces on a wound bed to accelerate healing of a wound, including a pressure chamber having a substantially airtight plunger and an inlet fluidly connected to a first end of a conduit. A constant force spring is operatively connected to apply a constant force to the plunger. A suction cup is in fluid communication with a second end of the conduit.

A valve can be provided in the conduit so as to be in fluid communication with the inlet of the pressure chamber and with the suction cup. The valve can be configured and adapted to be switched from a first position to a second position. In the first position, the suction cup is in fluid communication with the pressure chamber to apply a substantially constant pressure to a wound bed within the suction cup. In the second position, the suction cup and the inlet of the pressure chamber are in fluid isolation, and the inlet of the pressure chamber can freely vent to the surroundings. The second position can be used to recharge the device and/or remove fluids/liquids from the device.

In another embodiment, the apparatus further includes a manifold in the conduit in fluid communication with the pressure chamber. In this embodiment, a pressure reserve is in fluid communication with the manifold. The pressure reserve and manifold can be configured and adapted to replenish the pressure in the pressure chamber as needed to maintain a substantially constant pressure in the pressure chamber.

The constant force spring can be structured to act along a common axis of motion with the plunger. It is also contemplated that the apparatus can include pulley means operatively connected to the plunger and to the constant force spring. The pulley means can communicate forces from the constant force spring acting along a first axis to the plunger acting along a second axis. Any other suitable configuration for providing a constant force from the spring to the plunger can also be used.

In further accordance with the invention, an apparatus is provided for generating constant cyclical micromechanical forces on a wound bed to accelerate healing of a wound. The apparatus includes a first pressure chamber configured and adapted to maintain a first substantially constant pressure. The first pressure chamber includes a fluid inlet operatively connected to the manifold. A second pressure chamber is configured and adapted to maintain a second substantially constant pressure. The second pressure chamber includes a fluid inlet and is operatively connected to the manifold. Switching means are operatively connected with the manifold and fluidly connected to a suction cup. The switching means are configured and adapted to alternate fluid communication between the first and second pressure chambers to apply a pressure to the suction cup that alternates between the first and second substantially constant pressures.

The apparatus can further include a self-winding mechanical power source operatively connected to actuate the switching means. The switching means can also be powered by an electrical power source, manually actuated power source, mechanical power source, or any other suitable power source.

These and other features and benefits of the insert of the subject invention and the manner of accelerating wound healing will become more readily apparent to those having ordinary skill in the art from the following enabling description of certain embodiments of the subject invention taken in conjunction with the several drawings described below.

BRIEF DESCRIPTION OF THE DRAWINGS

So that those skilled in the art to which the subject invention appertains will readily understand how to make and use the devices and method for applying micromechanical therapy according to the subject invention without undue experimentation, certain embodiments thereof will be described in detail hereinbelow with reference to certain figures, wherein.

DETAILED DESCRIPTION OF A SPECIFIC EMBODIMENT

Figure 1:
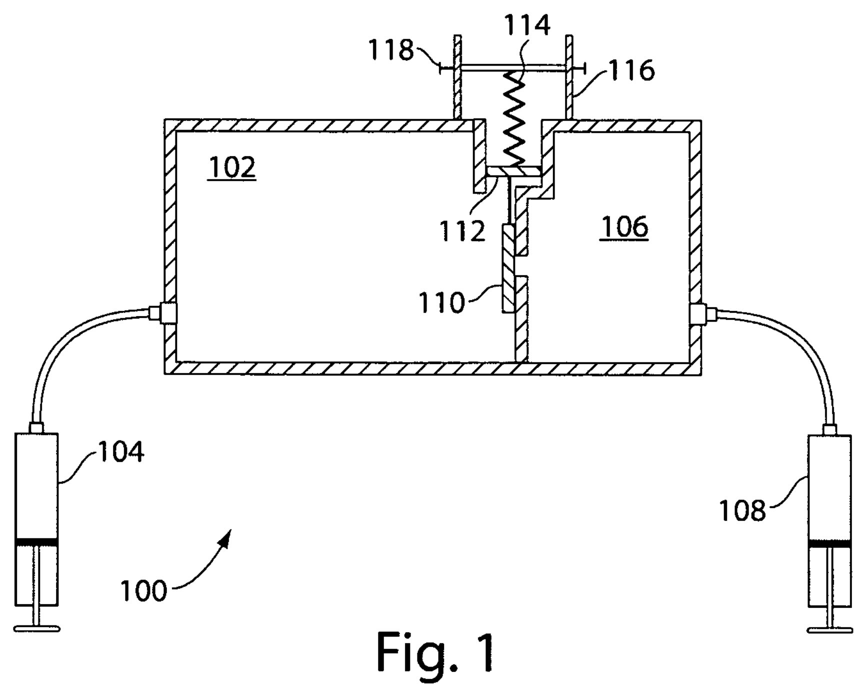
FIG. 1 is a schematic view of a representative embodiment of an apparatus for providing micromechanical forces on a wound bed in accordance with the present invention, showing the first and second chambers with a spring loaded plunger-actuated door for regulating pressure therebetween.

Referring now to the drawings, wherein like reference numerals identify or otherwise refer to similar structural features or elements of the various embodiments of the subject invention, there is illustrated in FIG. 1 an exemplary apparatus for providing micromechanical forces on a wound bed to accelerate healing of a wound designated generally by reference character 100.

FIG. 1 shows an exemplary embodiment of an apparatus 100, which includes a first pressure chamber 102 communicating with a first vacuum source 104. The first pressure chamber also communicates with a suction cup, which is not shown in the schematic view of FIG. 1, but see e.g., FIG. 3. A second pressure chamber 106 communicates with a second vacuum source 108. The second pressure chamber 106 is operably connected with the first pressure chamber 102 through a mechanical door 110. A plunger 112 is in fluid contact with the first chamber 102 on one side, and in fluid contact with the surrounding atmosphere on the other side so as to be moveable in reaction to changes of pressure in chamber 102. Plunger 112 is operatively connected to door 110. The plunger 112 is configured and adapted to maintain a substantially constant pressure in the first chamber 102 by moving the door between a first position and a second position.

When starting the apparatus in operation, vacuum source 104, shown as a syringe, can be drawn out to provide the desired level of vacuum in chamber 102. This action will also simultaneously close door 110. When door 110 is in the closed position, the first and second chambers are in fluid isolation from one another. This allows for vacuum source 108, also shown as a syringe, to be drawn out to provide an even greater level of vacuum for chamber 106 than in chamber 102. It is preferable that the initial pressure in chamber 106 be significantly lower than the initial pressure in chamber 102, so that chamber 106 can act as an effectively infinite vacuum when door 110 opens. Plunger 112 and door 110 are configured to move in response to pressure changes in chamber 102, but to be independent of the pressure in chamber 106. This allows chamber 106 to be evacuated significantly below the treatment pressure in chamber 102, which allows "storage" of vacuum pressure for use in maintaining the treatment pressure in chamber 102.

Vacuum source 104 provides negative pressure or suction to the first chamber 102, and in turn to a suction cup sealed to a wound bed. As the wound bed drains into the suction cup, or as other pressure losses occur, the pressure within first chamber 102 builds slightly. As the pressure gradually builds in chamber 102, the building pressure acts on plunger 112 and moves plunger 112 in cooperation with the force provided by spring 114. As plunger 112 moves outward, it slides door 110 in the same direction until the port under door 110 is uncovered to allow fluid communication between chamber 102 and chamber 106. This allows building pressure from chamber 102 to be released into chamber 106.

As pressure is released from chamber 102 into chamber 106, the pressure force acting inward on plunger 112 increases. As the increasing inward pressure force overcomes the force of spring 114, plunger 112 moves back inward in chamber 102. Door 110 returns with plunger 112 until the port between chambers 102 and 106 is sealed once again. At this point, the treatment pressure is restored in chamber 102, and therefore also at the wound bed in the suction cup.

The process repeats, as pressure is gradually lost again in chamber 102. Eventually the vacuum pressure in both chambers 106 and 108 will be diminished and must be reset. With door 110 closed, chamber 106 can be re-evacuated as needed without affecting the substantially constant pressure at the wound bed. However, between charging of vacuum source 108, apparatus 100 operating in the manner described above maintains a substantially constant pressure on the suction cup using only mechanical feedback (no gages or electronic sensors) to control pressure. Optionally, a simple modification can include a timer or sensor that sounds an alarm when the device needs to be reset.

Spring 114 is preferably a variable force spring attached to a structure 116 that allows for adjustment of the tension in spring 114 by raising or lowering adjustment bolts 118. The spring tension can be set in this manner to increase or decrease the constant pressure at the wound bed as needed. Exemplary pressures include 125 mmHg, 150 mmHg, 175 mmHg, or any other suitable pressure (these are absolute pressures where atmospheric pressure is generally around 760 mmHg). A constant force spring could optionally be used. However, the adjustability would be limited.

While spring 114 provides the advantages of adjustability, those skilled in the art will recognize that spring 114 is optional, as plunger 112 can be configured to have proper motion in response to the volumetric changes in chamber 102 without a spring. For example, plunger 112 can be connected to (or be part of) a pneumatic chamber in lieu of spring 114. In short, any suitable spring means can be used without departing from the spirit and scope of the invention.

Vacuum source 104 is also optional. When initializing apparatus 100 without vacuum source 104, vacuum source 108 evacuates chambers 102 and 106 together until door 110 closes, since by design door 110 is configured to close when chamber 102 is at the desired treatment level. Further pumping of source 108 after door 110 closes will lower the pressure of chamber 106 below the treatment pressure without increasing the suction on the wound bed beyond the treatment pressure.

Furthermore, any suitable mechanism can be used in lieu of spring 114, plunger 112, and door 110. It is possible to use any suitable relief valve to regulate the treatment pressure. Moreover, any mechanism can be used without departing from the spirit and scope of the invention as long as it 1) cuts off fluid communication between the wound bed and the pressure reserve when the wound bed drops to treatment pressure; 2) allows further evacuation of the pressure reserve without further lowering the pressure on the wound bed; and 3) brings the pressure reserve back into fluid communication with the wound bed until treatment pressure is restored at the wound bed if the pressure at the wound bed rises above a tolerable threshold. In this manner, a substantially constant pressure at the wound bed is maintained that oscillates only between the desired treatment pressure and a tolerable pressure increase above the desired pressure, which is required to move the mechanism to restore the desired treatment pressure.

Figure 2:
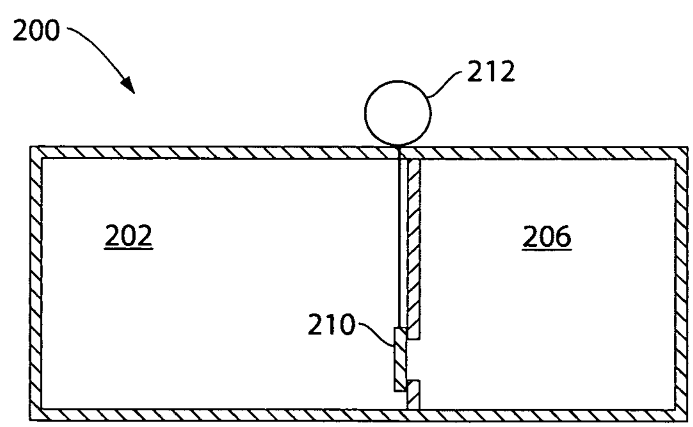
FIG. 2 is a schematic view of another representative embodiment of an apparatus for providing micromechanical forces on a wound bed in accordance with the present invention, showing the sensing and actuating means for moving the door to regulate pressures in the pressure chambers.

FIG. 2 shows apparatus 200 that is similar in most respects to the apparatus 100 shown in FIG. 1. In lieu of using a pressure-actuated plunger to move mechanical door 210 to regulate the pressure in chamber 202, an electrical control unit 212 is provided. Control unit 212 includes sensors, an actuator for moving door 210, and control system for controlling door 210. Control unit 212 maintains a substantially constant pressure in the first chamber 202 by moving the door between the first and second positions described above. When control unit 212 senses the pressure in chamber 202 has risen above a desired level, control unit 212 actuates door 210 to open the port between chambers 202 and 206 to restore the proper pressure to chamber 202. Those skilled in the art will readily appreciate that any suitable sensing and actuating means can be used, including any suitable combination of electrical or mechanical sensors, control systems, motors, and/or actuators.

Figure 3:
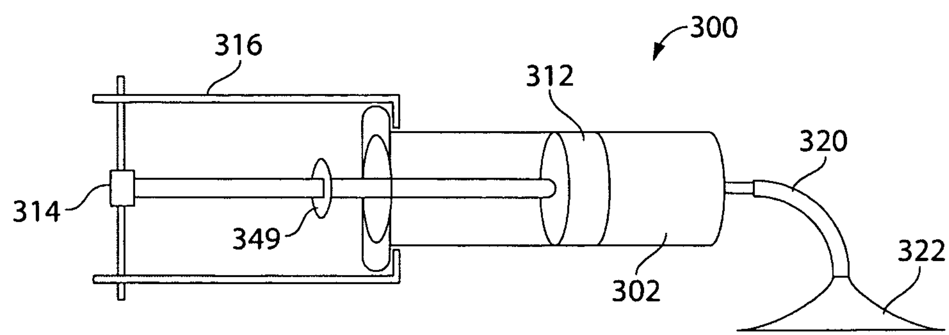
FIG. 3 is a perspective view of another representative embodiment of an apparatus for providing micromechanical forces on a wound bed in accordance with the present invention, showing a constant force spring mounted to provide constant force to a pressure chamber and thereby provide a constant pressure to a suction cup.

FIG. 3 shows another apparatus 300 in accordance with the present invention. Apparatus 300 includes a pressure chamber 302 having a substantially airtight plunger 312 at one end. At the other end of pressure chamber 302, a chamber inlet is fluidly connected to a first end of a conduit 320. A constant force spring 314, mounted to a support structure 316 is connected to plunger 312 to apply a constant force thereto. A suction cup 322 is in fluid communication with a second end of conduit 320. Grip 349 allows for manual resetting of plunger 312 when it reaches its maximum extent of travel.

In operation, suction cup 322 is sealed to a wound bed with plunger 312 positioned near the inlet end of pressure chamber 302. As fluids enter the system, which would otherwise raise the pressure in chamber 302, constant force spring 314 attached to a support structure 316 pulls plunger 312 away from conduit 320. This action expands pressure chamber 302 to maintain a constant pressure. The constant spring force developed by spring 314 controls the pressure levels maintained in pressure chamber 302 without any need for gages. Thus, the properties of spring 314 can be varied by design, as is known in the art of constant force springs, in order to create a particular pressure level for chamber 302.

Figure 4:
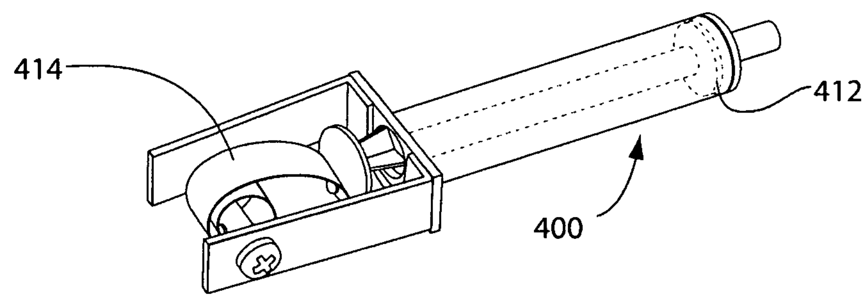
FIG. 4 is a perspective view of a portion of another representative embodiment of an apparatus for providing micromechanical forces on a wound bed in accordance with the present invention, showing a constant force spring structure having a short axis configuration.
Figure 5:
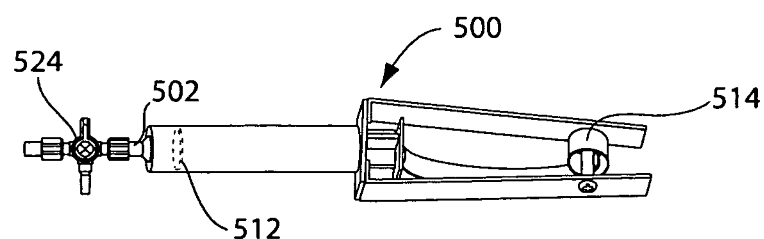
FIG. 5 is a perspective view of a portion of another representative embodiment of an apparatus for providing micromechanical forces on a wound bed in accordance with the present invention, showing a constant force spring structure having a long axis configuration.

FIG. 4 shows an apparatus 400 that is similar in most respects to apparatus 300 described above. Spring 414 acts in the same axis of motion as the movement of plunger 412. Apparatus 400 has a relatively short axis of motion for spring 414. FIG. 5 shows a similar apparatus 500 having a longer axis of motion for spring 514. Those skilled in the art will readily appreciate that any length or configuration of spring can be used as long as the force provided is substantially constant.

When plunger 512 has traveled to the end of its axis of motion, it must be reset, e.g., manually, to maintain a substantially constant negative pressure gradient at the wound bed. The short axis configuration shown in FIG. 4 is advantageous because it is compact, and is well suited to treatment of smaller wounds that heal quickly or have relatively low amounts of fluid discharge. However, the longer axis configuration shown in FIG. 5 provides longer duration of constant pressure before the pressure needs resetting. Those skilled in the art will readily appreciate that any suitable axis of motion length can be tailored for a specific application without departing from the spirit and scope of the invention.

As shown in FIG. 5, a valve 524 is provided in fluid communication with pressure chamber 502 of apparatus 524. Valve 524 can be connected to a conduit (e.g., 320 in FIG. 3) so as to be in fluid communication with the inlet of pressure chamber 502 and with a suction cup (e.g., 322 in FIG. 3). Valve 524 is configured to be switched from a first position to a second position. In the first valve position, the suction cup is in fluid communication with the pressure chamber to apply a substantially constant pressure to a wound bed within the suction cup. In the second position, the suction cup and the inlet of pressure chamber 502 are in fluid isolation, and the inlet of pressure chamber 502 can freely vent to the surroundings. A valve such as valve 524 could optionally be connected to a fluid collection chamber so that if fluid has collected in the pressure chamber, the fluid can be emptied into the collection chamber when the vacuum is being re-applied, for example during dressing changes. Those skilled in the art will appreciate that valve 524 is optional, and moreover, any other suitable valve configuration can be used without departing from the spirit and scope of the invention.

Figure 6:
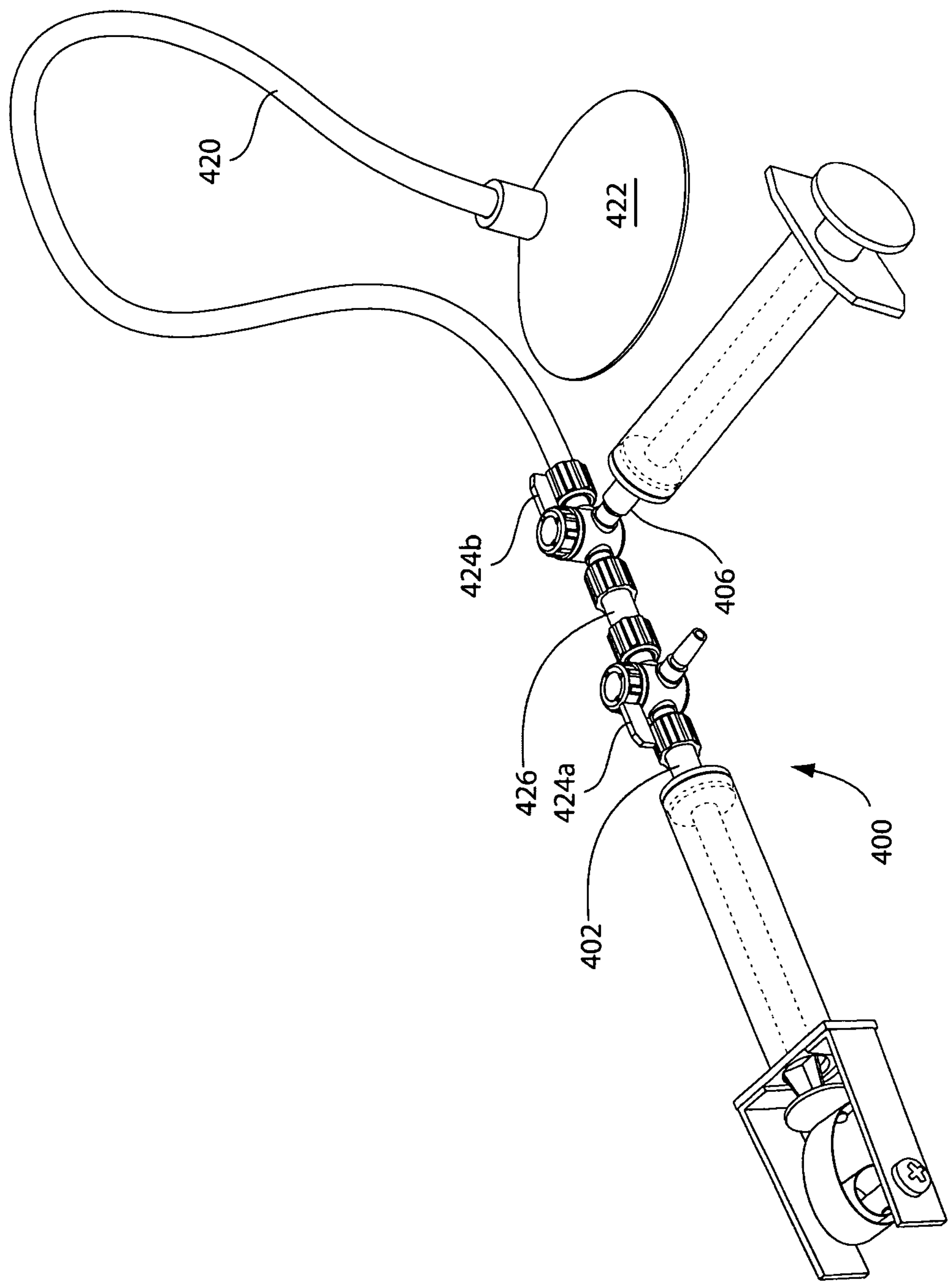
FIG. 6 is a perspective view of the apparatus of FIG. 4 in accordance with the present invention, showing a manifold with a second pressure chamber that provides a pressure reserve or pump for the main pressure chamber.

As shown in FIG. 6, apparatus 400 further includes a manifold 426 in conduit 420 in fluid communication with pressure chamber 402 and suction cup 422. In this embodiment, a pump or pressure reserve 406 is also connected in fluid communication with manifold 426. Pressure chamber 402 and pressure reserve 406 connect to manifold 426 through valves **424*a* and 424*b*, similar to valve 524 described above. Pressure reserve 406 and manifold 426 are configured to pump or recharge the vacuum pressure in the pressure chamber 402 to maintain a substantially constant pressure in suction cup 422. When spring 414 is near the end of its axis of travel, pump/reserve 406 can be used in conjunction with valves 424*a,b* to pump chamber 402 so spring 414 returns to the beginning of its axis of travel. Pump 406 can be permanently attached to manifold 426, or can be configured to attach to manifold 426** only when needed for pumping.

To pressurize apparatus 400, valve **424*b* can be rotated to place pressure reserve 406 in fluid communication with chamber 402. Then the plunger of pressure reserve 406 can withdrawn. Valve 424*a* can then be rotated to vent to the atmosphere. Next, the plunger of pressure reserve 406 can be advanced back toward valve 424*b* to vent reserve 406 through valve 424*a*, and valve 424*a* can be rotated to back to place chamber 402 in fluid communication again with suction cup 422. These steps can be repeated as needed to completely recharge pressure chamber 402 with spring 414. FIG. 5 shows a similar configuration as that shown in FIG. 4, having constant force spring 514, manifold 526, and reserve 506, with long axis apparatus 500, in lieu of the short axis configuration shown in FIG. 4**.

Figure 8:
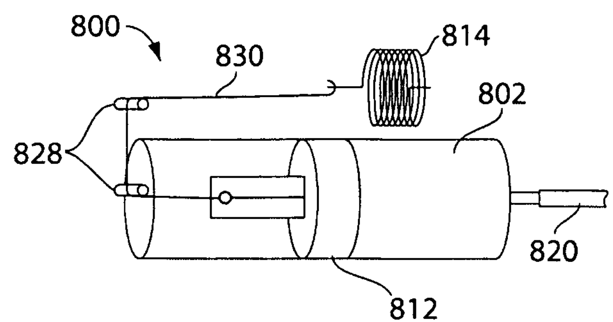
FIG. 8 is a perspective view of a portion of another representative embodiment of an apparatus for providing micromechanical forces on a wound bed in accordance with the present invention, showing a constant force spring configured to act through a pulley structure on the plunger of the pressure chamber.

The constant force spring can be structured to act along a common axis of motion with the plunger, as described above. It is also contemplated that the apparatus can include pulley means to communicate forces from a constant force spring acting along a first axis to a plunger acting along a second axis. Apparatus 800, shown in FIG. 8, includes a pair of pulleys 828 that operatively connect plunger 812 to spring 814 via cable 830. One pulley 828 is substantially in line with the axis of motion of plunger 812. The other pulley 828 is offset to the side of chamber 802 to be substantially in the line of motion of spring 814. In this configuration, constant force spring 814 can apply a constant force to plunger 812 to supply a substantially constant pressure to chamber 802 and conduit 820, much as described above, except that the axis of motion of spring 814 is offset from the axis of motion of plunger 812.

This configuration is shorter in length and can be less bulky than other configurations. For example, it is possible for apparatus 800 using pulleys to provide the same long axis of motion as provided in long axis configuration 500, while having a significantly shorter overall length of the apparatus. Those skilled in the art will readily appreciate that any other suitable configuration for providing a constant force from the spring to the plunger can also be used without departing from the spirit and scope of the invention.

Figure 9:
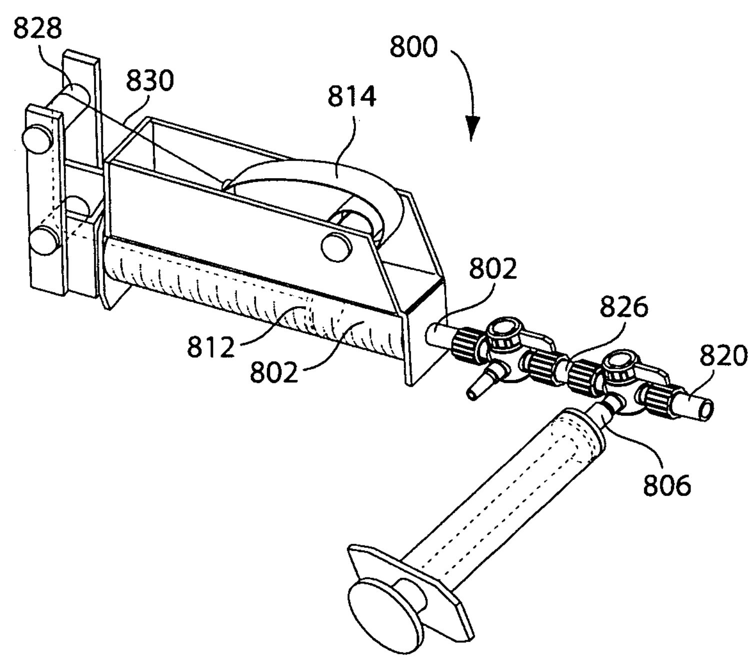
FIG. 9 is a perspective view of a portion of the apparatus of FIG. 8 in accordance with the present invention, showing the pulley system, constant force spring, and pressure chamber connected to a manifold with a reserve pressure chamber.
Figure 10:
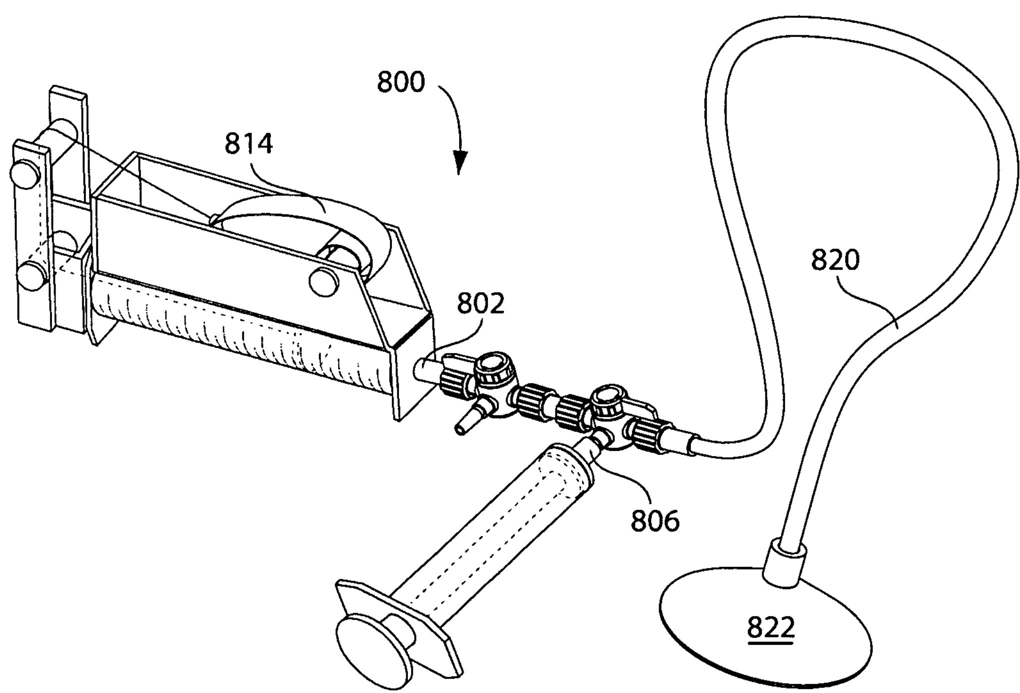
FIG. 10 is a perspective view of the apparatus of FIG. 8 in accordance with the present invention, showing the suction cup and conduit connected to the manifold.
Figure 11:
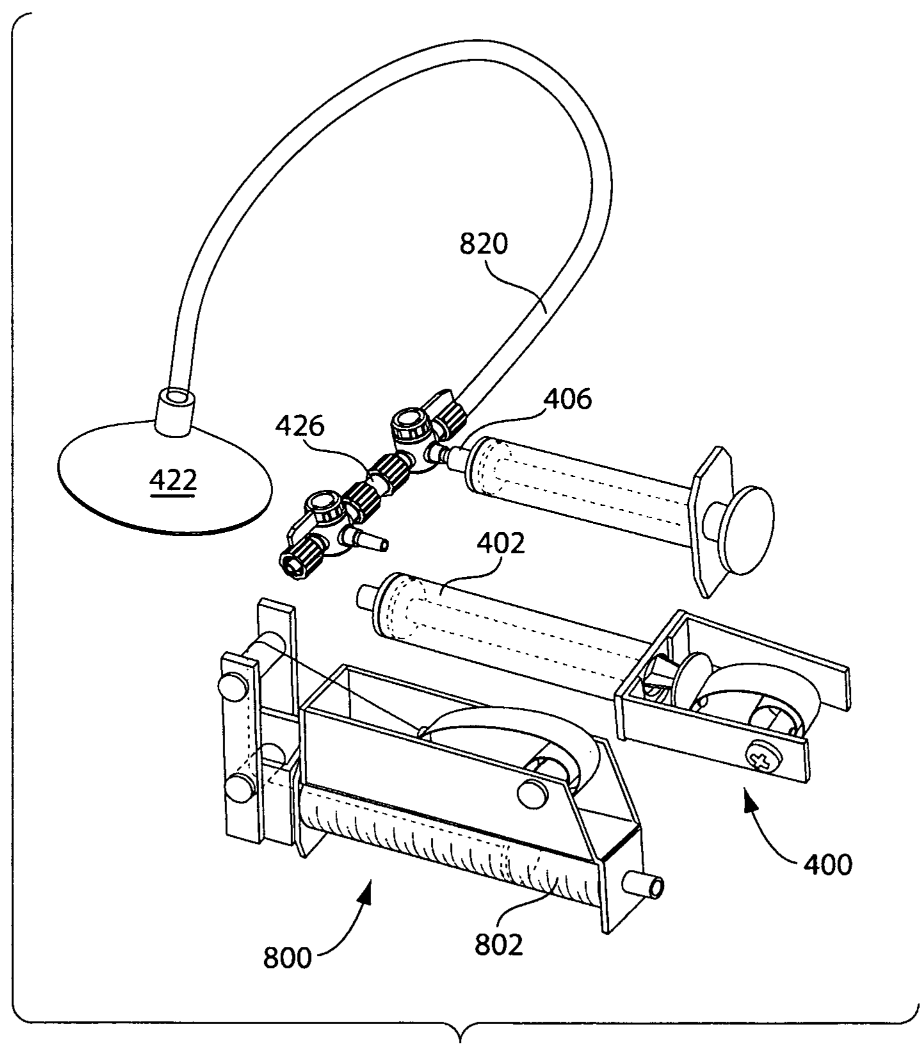
FIG. 11 is perspective view of a portion of the apparatus of FIG. 9 in accordance with the invention, next to a portion of the apparatus of FIG. 4 in accordance with the present invention, showing the relative size between the two embodiments.

As shown in FIGS. 9 and 10, apparatus 800 can be used in conjunction with a manifold 826, pressure reserve 806, conduit 820, and suction cup 822 that work as described above with reference to FIGS. 6 and 7. FIG. 11 shows apparatus 800 next to apparatus 400 for a comparison of overall length. Apparatus 800 is shorter in length than apparatus 400, while having a longer axis of motion available, thus requiring less frequent resetting to maintain pressure.

The force generated by a constant force spring in this application must be matched to the plunger size and desired constant pressure for wound therapy. Exemplary configurations include spring constants of k=0.17 lbf, k=0.57 lbf, and k=0.97 lbf for pressure chambers (syringes) of volumes V=3.0 cc, V=10.0 cc, and V=20.0 cc, having plunger areas of A=0.07 $in^2$, A=0.24 $in^2$, and A=0.40 $in^2$, respectively. Each of these examples provides a therapy pressure of approximately P=125 mmHg.

It is advantageous for the apparatus to be actuated with one hand when resetting pressures. Those skilled in the art will readily appreciate how to use variations of the apparatus for use with single-handed or double handed actuation without departing from the spirit and scope of the invention.

Figure 12:
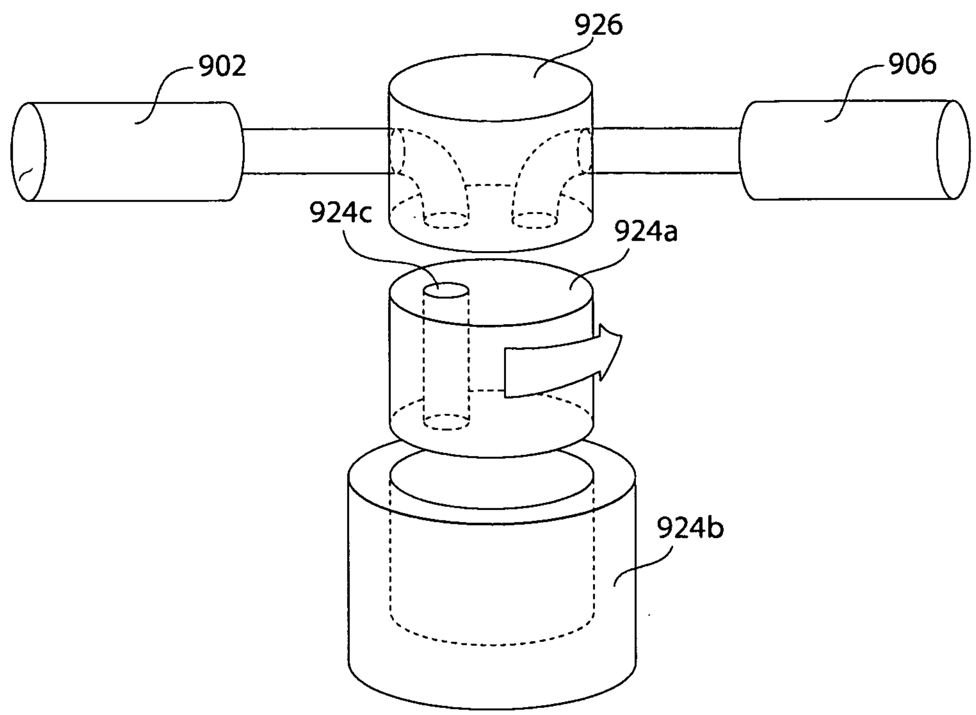
FIG. 12 is a schematic view of a portion of a representative embodiment of an apparatus for providing constant cyclical micromechanical forces on a wound bed in accordance with the present invention, showing the rotating valve assembly for alternating pressures on a wound between a high pressure chamber and a low pressure chamber.

While substantially constant negative pressure on a wound bed can accelerate healing of the wound, it has also been proven that application of negative pressures that vary in a repeated cycle can be even more effective. FIG. 12 shows apparatus 900, which is configured to generate a constant cyclical micromechanical force on a wound bed. Apparatus 900 includes a first pressure chamber 902 configured and adapted to maintain a first substantially constant pressure level below atmospheric pressure, much as the pressure chambers described above. First pressure chamber 902 includes a fluid inlet operatively connected to manifold 926. A second pressure chamber 906 is configured and adapted to maintain a substantially constant pressure that is even lower than the pressure of chamber 902. The second pressure chamber includes a fluid inlet and is operatively connected to the same manifold 926. A valve connected to manifold 926 includes outer casing **924*b* containing rotating valve 924*a* that alternates between high and low pressure chambers 902, 906** on one end, while always being in fluid communication with the suction cup on the other end.

Valve **924*a* thus provides for alternating fluid communication between pressure chambers 902/906 and a suction cup (not shown, but see suction cup 322 in FIG. 3). Valve 924*a* is configured to rotate within casing 924*b* to position passage 924*c* in fluid communication with chambers 902 and 906 one at a time. The other end of passage 924*c* can be configured to communicate with a suction cup at all times. Since the respective pressures of chambers 902 and 906 are at different levels, as valve 924*a* rotates, it provides a cyclical pressure variation between the first and second pressure chambers to apply pressure to a wound bed that alternates between two substantially constant levels. While shown as a circular passage in the schematic of FIG. 12, passage 924*c* can be of any suitable shape. For example, it is possible for passage 924***c* to have the shape of a wedge (or a half solid interior) so that at exactly one pressure chamber 902/906 is fluidly connected to the suction cup at a time.

If one pressure source, e.g., 906 is set to the extended position, i.e. the plunger is pushed in, and the other pressure source, e.g. 902 is set to the unextended position, i.e. the plunger is pulled out near its maximum extent, and if passage 924*c* starts in communication with chamber 902, the wound will be at the pressure of chamber 902. As valve 924*a* rotates, it will block chamber 902 off from the suction cup and bring passage 924*c* into communication with chamber 906. Assuming for this example that chamber 906 uses a constant force spring as described above to provide a stronger vacuum than chamber 902, the plunger of chamber 906 will be drawn back by its spring to create increased suction at the wound site.

Then, as valve 924*a* rotates back to connect passage 924*c* with chamber 902, the plunger of chamber 902 will move toward valve 924*a*, giving off some of its air to the wound, which was at the lower pressure level of chamber 906. As valve 924*a* continues to rotate, the plungers of chambers 902, 906 will move in the same manner, moving air from chamber 902 to chamber 906 little by little. As the process continues and as pressure losses occur, one or more of the plungers will reach the end of the respective pressure chamber. In order to maintain the treatment pressure regime, the pressure chambers can be reset, as described above with respect to constant pressure embodiments.

A standard stopcock can be adapted for use as a rotating valve. A typical stopcock requires a constant torque of approximately 1.125 lbf-in to rotate at a substantially constant rate of two seconds per cycle. Using a spring motor with a 0.5-inch radius and an unwound length of 100 inches, an input torque of 63.3 lbf-in is necessary to rotate the stopcock at this rate for about one hour. A gear box 951 (see FIG. 13) allows reduction of the large torque to the desired 1.125 lbf-in needed to drive the stopcock.

Figure 13:
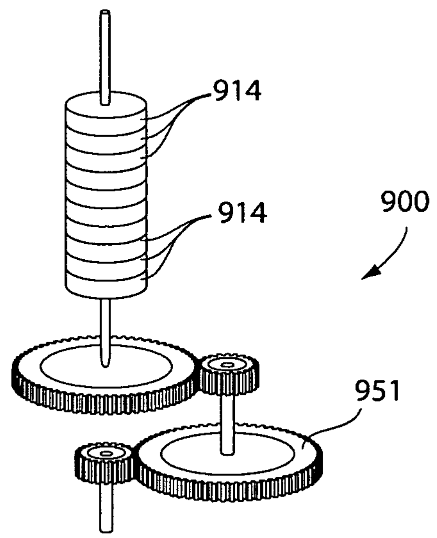
FIG. 13 is a schematic view of a portion of a representative embodiment of an apparatus for providing micromechanical forces on a wound bed in accordance with the invention, showing the stack of springs connected to a gear chain for providing torque to the rotating valve assembly of FIG. 12.

The following provides an explanation of how to design an exemplary four-gear chain, as depicted in FIG. 13. Since the linear velocity (rotational velocity times radius) of two gears (e.g., g1 and g2) at their point of interaction is equal, the angular velocity of each gear multiplied by its respective radius can be set equal to each other as shown in equations the following equations:

$$\omega_{g1}r_{g1}=\omega_{g2}r_{g2};\text{ and}$$

$$\omega_{g3}r_{g3}=\omega_{g4}r_{g4}.$$

Linking gears 2 and 3 together will cause their angular velocities to be equal to each other. The corresponding substitution and simplifications result in:

$$\omega_{g1}=(r_{g2}/r_{g1})(r_{g4}/r_{g3})\omega_{g4}.$$

Using the same procedure used to determine this equation, multiplying the force of each gear by its radius will determine the torque of the gear. Since the torques for gears g2 and g3 are equal, a substitution can be made again to give the following:

$$\tau_{g3}=\tau_{g2};\text{ and}$$

$$\tau_{g1}=(r_{g1}/r_{g2})(r_{g3}/r_{g4})(1/\text{eff}_1)(1/\text{eff}_2)\tau_{g4},$$

where $\text{eff}_1$ and $\text{eff}_2$ are the efficiencies with which the torque transfer takes place at the contacts of the two respective gears. To determine the speed necessary for a spring motor to unwind in a specific span of time, equation $v=2\pi rn/\text{time}$ was used, where r is the torque spring radius and n is the number of windings. This time can also be related to the angular velocity of the gears provided by: $\text{time}=2\pi n/\omega_{g1}$. These equations allow for determination of the spring torque required given required turning torque for the stopcock, duration, and rate of turning. This allows generally for system design given the input requirements.

Constant torque is preferable, in order to maintain a constant rate of pressure cycling. To avoid using a much larger spring to achieve this torque, the design shown in FIG. 13 uses 10 spring motors 914 in parallel to provide the necessary torque. In this example, each spring motor has an input torque of 6.5 lbf-in. However, those skilled in the art will readily appreciate that this is exemplary only, and that any suitable configuration can be used to supply the torque without departing from the spirit and scope of the invention.

Those skilled in the art will readily appreciate that any suitable structure for providing alternating connections to the two pressure chambers can be used without departing from the spirit and scope of the invention. Also, while apparatus 900 has been described as having two substantially constant pressure sources, those skilled in the art will readily appreciate that three or more pressure sources can be used without departing from the spirit and scope of the invention.

Apparatus 900, can advantageously include a self-winding mechanical power source to provide power to actuate rotating valve 924*a*. The spring(s) 914 are linked on one side to gear chain 951 to provide constant driving torque to valve 924*a*. On the other side spring(s) 914 are connected to a freely oscillating, weighted rotor through a ratcheting mechanism to wind and tighten spring(s) 914 in response to ordinary body movements, as is known in the art of self-winding mechanisms.

When a patient wears apparatus 900, ordinary body movements, such as walking, breathing, rolling over in sleep, etc., throughout the day can provide power for the rotation of valve 924*a*, without needing to remember to wind or charge any motors or batteries. This is similar to the manner in which self-winding watches are powered by ordinary, routine motions of the wearer's arm throughout the day. Those skilled in the art will readily appreciate that self-winding mechanisms, while advantageous, are optional. Electrical power sources, manually actuated power sources, foot actuated power sources, mechanical power sources, or any other suitable power sources can be used without departing from the spirit and scope of the invention.

The various exemplary systems described above can provide pressure for micromechanical therapy with a low-cost disposable alternative to the known electrical pumps. This can potentially represent a cost to patients that is as low as one-one-hundredth of the daily cost of the previously available electrical pumps. Moreover, the hand-actuated embodiments described above are highly portable and are convenient to use. Generally, resetting of pressure chambers is only required once every 4-5 hours, which can be performed by healthcare professionals in a hospital, or by a patient not in a hospital.

Figure 7:
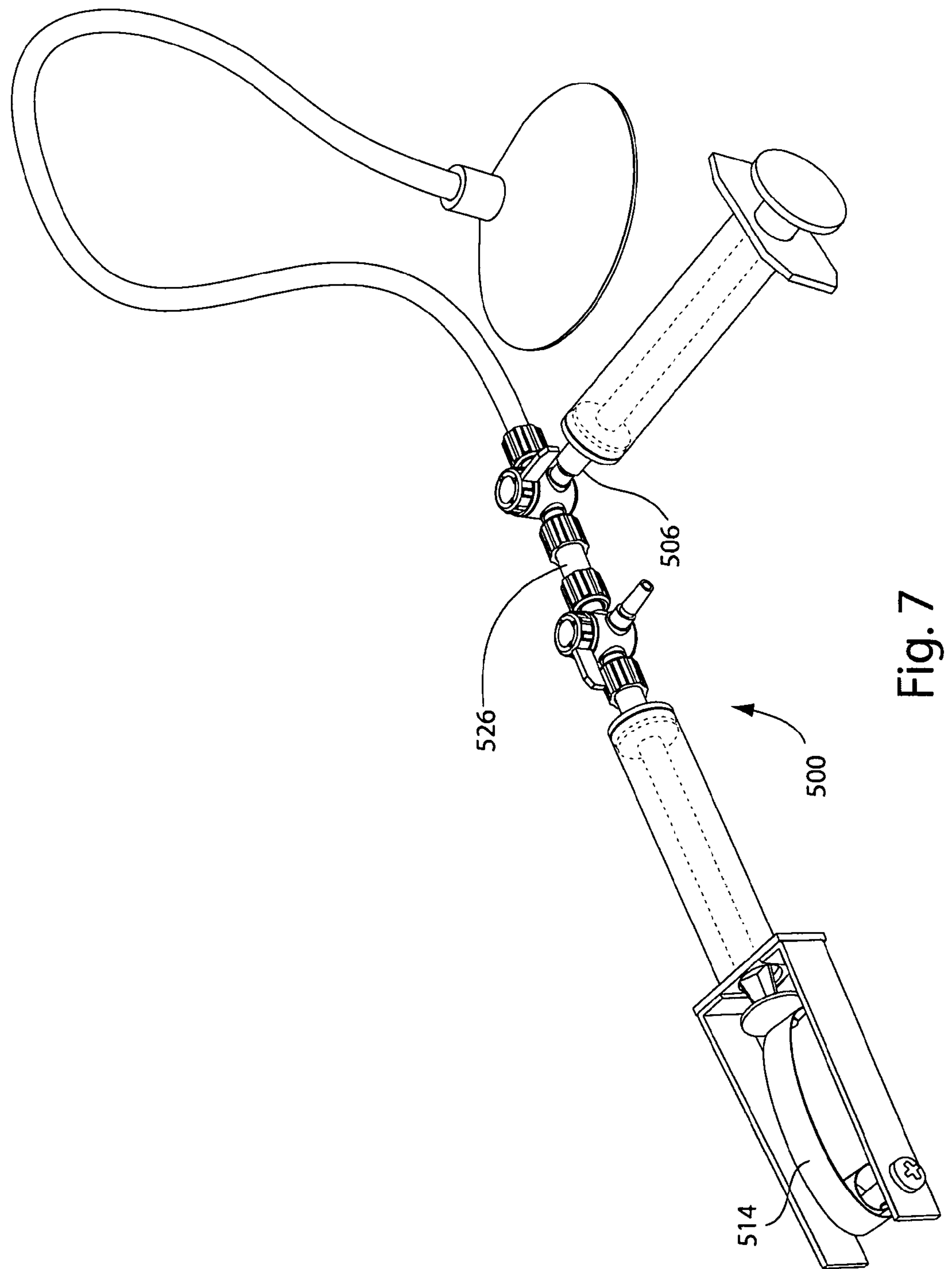
FIG. 7 is a perspective view of the apparatus of FIG. 5 in accordance with the present invention, showing a manifold with a second pressure chamber that provides a pressure reserve or pump for the main pressure chamber.

The vacuum can be applied through the connection of another syringe (see, e.g., FIGS. 6 and 7). By Pascal's Law, pressures are transmitted equally within a fluid. Thus, to make the vacuum application user friendly, which is particularly important for the very young or the elderly, a small diameter syringe should be used. The forces are reduced proportional to the cross section area of small diameter syringes. Further implementations of this device can use a lever that is attached to a syringe to allow for even more ease of use of the system.

In lieu of manually resetting the vacuums, the pressure chambers can also be reset constantly through the use of body motions. For example, a pump can be located under the padding in a shoe. This pump could apply a negative pressure, with connected tubes communicating the negative pressure from the foot to the application area each time the patient takes a step. Similarly, other types of body motions, such as those that occur when a person shifts while sleeping can also be taken advantage of to implement the vacuum pressures. Such embodiments reduce or eliminate the need for manual resetting of the pressure chambers, similar to the way valve 924*a*, described above, can be powered with self-winding mechanisms.

Known micromechanical therapy devices are heavy and cumbersome. One known type of device provides a constant vacuum through the use of weights applied to a syringe. The weights on this device have to be consistent with the vacuums applied. In a typical configuration, the necessary weights were approximately 2 kg (4.5 lbs). This is a substantial weight to be carried around by a patient.

Other known types of micromechanical therapy devices use an electronic pump to obtain the vacuum and keep that vacuum at a constant level. Such devices are generally sold as a portable unit. Electrical pump type devices are generally heavier than the embodiments of the invention described above. Another large drawback of this type of device is that the battery levels have to be monitored to know when a battery needs to be replaced or recharged. Devices powered by electrical outlets constrain the patient to remain near the power outlet. Further, if the battery dies, the power fails, or the patient is in a situation where power/batteries are unavailable (e.g. in the wilderness or battlefield), the patient is in jeopardy of losing the treatment for that duration.

The embodiments of micromechanical therapy devices of the invention are portable and relatively inexpensive because they do not require heavy and expensive batteries. Convenient portability allows a patient to be more mobile during the healing process, which also contributes to the healing process. Further, the devices of the invention are less intrusive and 'imposing' which also makes recovery faster because of psychological effects helping the patient feel less "sick" since he or she is not hooked up to motors or other cumbersome devices. Moreover, the simplicity of the invention allows for less monitoring by health care professionals when used in a hospital setting. The devices in accordance with the invention run less risk of electrocution and are also safer around children than previously known devices, since little or no electrical power is used (the power in the sensor embodiments, e.g., apparatus 200, is a fraction of that used in the known devices that use power to operate a large vacuum pump).

The devices in accordance with the invention can vary in size from a few centimeters to a few inches. Thus they are relatively small compared to known devices. One possible use of these devices is as bandages. The wound healing devices of the invention can be used for different types of wounds and cuts ranging from minor cuts to larger wounds. Since the devices of the invention do not require batteries, they are much more user friendly. Small size allows use as ubiquitous bandages replacing the passive bandages that have been in use for so many years.

The invention can be used in the field by paramedics. Possible uses include people who are camping or out in the wilderness where there is no access to batteries or weights. Where there is a suitably trained paramedic accompanying a group, the paramedic can use the device at his or her discretion depending on the size of the wound. Other settings for which the invention is well suited include application in athletics, nursing homes, in veterinary clinics, and in research applications, such as on animals for testing the efficacy and applicability of micromechanical force therapy.

Another setting for which the devices of the invention are particularly suited is in the battlefield. It is common for soldiers to be treated with micromechanical force therapy. However, currently the soldiers have to be flown in from the battlefield to the nearest hospital where the known forms of micromechanical therapy devices (requiring a wall vacuum outlet or an electronic vacuum generator) can be applied. However, the devices in accordance with the invention can simply be applied as a bandage.

The examples above have utilized syringes as pressure chambers. However, those skilled in the art will readily appreciate that pistons, bladders, or any other suitable pressure chambers can be used without departing from the spirit and scope of the invention. Similarly, any suitable pump can be used as a pressure reserve or vacuum source without departing from the spirit and scope of the invention.

Although the apparatus and methods of the subject invention have been shown and described with reference to certain embodiments, those skilled in the art will readily appreciate that various changes and/or modifications may be made thereto without departing from the spirit and scope of the subject invention as defined by the appended claims.

What is claimed is:

1. An apparatus for providing micromechanical forces on a wound bed to accelerate healing of a wound, the apparatus comprising:

a first pressure chamber communicating with a first vacuum source and with a suction cup;

a second pressure chamber communicating with a second vacuum source, the second pressure chamber being operably connected with the first pressure chamber through a door; and a plunger in fluid contact with the first chamber and operatively connected to the door, wherein the plunger is configured and adapted to maintain a substantially constant pressure in the first chamber by moving the door between:

i) a first position wherein the first and second chambers are in fluid communication with one another; and ii) a second position in which the first and second chambers are in fluid isolation from one another.

2. An apparatus for providing micromechanical forces on a wound bed to accelerate healing of a wound, the apparatus comprising:

a) a first pressure chamber communicating with a first vacuum source and with a suction cup;

a second pressure chamber communicating with a second vacuum source, the second pressure chamber being operably connected with the first pressure chamber through a door; and sensing and actuating means configured and adapted to maintain a substantially constant pressure in the first chamber by moving the door between:

i) a first position when the first pressure chamber is at an elevated pressure to place the first and second chambers in fluid communication with one another; and ii) a second position in which the first and second chambers are in fluid isolation from one another.

3. An apparatus for generating constant cyclical micromechanical forces on a wound bed to accelerate healing of a wound, the apparatus comprising:

a) a first pressure chamber configured and adapted to maintain a first substantially constant pressure, the first pressure chamber including a fluid inlet operatively connected to a manifold;

b) a second pressure chamber configured and adapted to maintain a second substantially constant pressure, the second pressure chamber including a fluid inlet operatively connected to the manifold; and c) a switching means operatively connected with the manifold and fluidly connected to a suction cup, the switching means being configured and adapted to alternate fluid communication between the first and second pressure chambers to apply an alternating pressure between the first and second substantially constant pressures to the suction cup.

4. An apparatus as recited in claim 3, further comprising a self-winding mechanical power source operatively connected to actuate the switching means.

* * * * *